US00PP08263P

United States Patent [19]

Dehan

[11] Patent Number: Plant 8,263

[45] Date of Patent: Jun. 15, 1993

[54] IMPATIENS PLANT NAMED DANHILL

[75] Inventor: Klara Dehan, Holon, Israel

[73] Assignee: Danziger - "Dan" Flower Farm, Moshay Mishmar Hashiva, Israel

[21] Appl. No.: 743,127

[22] Filed: Aug. 9, 1991

[51] Int. Cl.[5] ..... A01H 5/00

[52] U.S. Cl. ..... Plt./87.6

[58] Field of Search ..... Plt./87.6

*Primary Examiner*—James R. Feyrer

*Attorney, Agent, or Firm*—Foley & Lardner

[57] ABSTRACT

A distinct cultivar of Impatiens plant named Danhill, characterized by its large, intense bright red flowers, dark green foliage with yellow variegation in and near the midrib and its continuous and abundant flowering.

1 Drawing Sheet

The present invention relates to a new and distinctive cultivar of Impatiens plant, botanically known as Impatiens, and known by the cultivar name Danhill. Danhill was developed by me through controlled breeding by crossing the cultivar identified by breeding number F-41 as the female parent with the cultivar identified as 96-16 as the male parent. Both parents are unreleased, proprietary lines.

Asexual reproduction of Danhill by cuttings taken by applicant at Mishmar Hashiva, Israel, has shown that the unique features of this new Impatiens are stabilized and are reproduced true to type in successive propagations. The cuttings preferably comprise tip cuttings with at least one axillary bud, which is vegetative and not a flower bud.

The following characteristics distinguish the new Impatiens from both its parent varieties and other cultivated Impatiens of this type known and used in the floriculture industry:

1. Flowers are very bright red.
2. Variegated foliage, with its leaves being dark green, with lighter variegation occurring at the midrid and areas around the midrid.
3. Flowers are relatively large in diameter.
4. Continuous and abundant flowering.
5. Stems are green infused with purple.
6. All the characters together are different from other varieties.

The accompanying color photographs illustrate the overall appearance of this cultivar, showing the colors as true as it is reasonably possible to obtain in a colored reproduction of this type.

The photo at the top of the sheet illustrates in top perspective view the foliage and flowers of a portion of a plant of Danhill.

The lower photo is a more enlarged showing of the flowers and foliage.

The following is a detailed description of my new Impatiens cultivar based on plants produced under commercial practice in the spring in Mishmar Hashiva, Israel.

Color references are made to The Royal Horticultural Society Colour Chart except where general terms of ordinary dictionary significance are used.

Parentage:

*Male parent.*—96-16.

*Female parent.*—F-41.

Propagation:

A. *Type cutting.*—Tip cuttings with at least one axillary, vegetative bud.

B. *Time to initiate roots.*—8–10 days both at 25°–30° C. summer, and 20°–22° C. winter.

C. *Rooting habit.*—Good root initiation.

Plant description:

A. *Form.*—Medium tall, mounted, symmetrical.

B. *Habit of growth.*—Compact to semi-erect, with good branching.

C. *Foliage description.*—(1) Size: Relatively large, approximately 11 cm long by 4.0 cm wide. (2) Shape: Oval, with acuminate tip. (3) Margin: Finely serrated. (4) Main color: Young foliage top side 137B; under side 147B. Mature foliage top side 147B; under side 147B. (5) Venation: Variegated color: Not precisely shown in R.H.S. Colour Chart, closest to 150D, somewhat lighter than the color illustrated; variegation extends along midrib and in varying amounts laterally of the midrib.

Flowering description:

A. *Flowering habits.*—From buds to open flower typically takes about five days.

B. *Natural flowering season.*—Natural flowering season is spring and summer in moderate climates. In Israel flowering also occurs in the winter.

C. *Flower bud description.*—Normal. Spurs up to 5.5 cm long on mature buds with throat originating from major sepal; the wide, oval part of the spur is 1.0 cm by 0.8 cm and close to 59C in color; the long part is approximately 4.5 cm in length, almost straight, and green 145A in color.

D. *Flowers borne.*—Flower buds are presented at the tips of stems overlying the terminal whorls of leaves. At most stems, there are generally about 4–5 buds in different stages of maturity, and normally about 1–2 or more open blooms, as the plant reaches market stage.

E. *Quantity of flowers.*—Total inflorescence is about 20–25 open flowers three months after planting. Flowering is continuous at temperatures above approximately 10° C. and with at least minimum levels of light.

F. *Petals.*—(1) Shape: Two pairs of petals are heart shaped, with each petal being approximately 3 cm from base to tip and slightly less at its widest point; the single flower is generally oval shape and larger being 0.4–0.5 cm in its major dimension. (2) Color: Top side in spring when opening 46A, with little or no fading. Under side near 47A. (3) Number of petals: Five. (4) Size of flowers: Large, approximately 6.0 cm in diameter.

G. *Reproductive organs.*—(1) Stamens: One in number. (a) Anther color: Green. (b) Pollen color: White. (2) Pistils: (a) Stigma: Cone shaped; green in color. (b) Style: Light green in color. (c) Ovaries: One in number; size 1.5 mm; color light green.

Disease resistance: None to date.

I claim:

1. A new and distinct cultivar of Impatiens named Danhill, as illustrated and described.

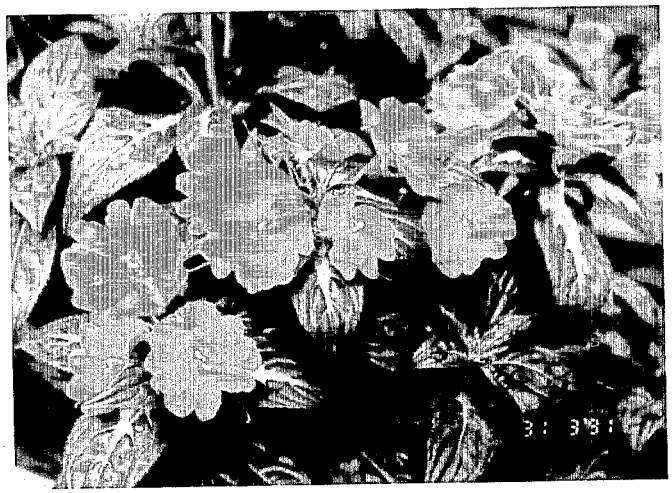
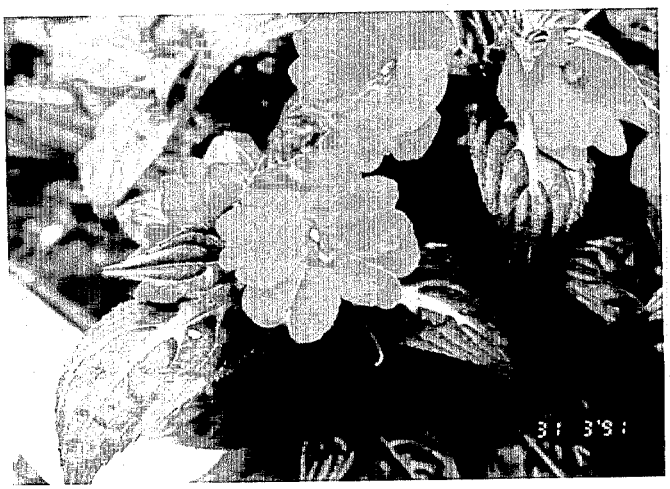

* * * * *